United States Patent
McCabe et al.

(10) Patent No.: US 8,401,639 B2
(45) Date of Patent: Mar. 19, 2013

(54) ANODAL STIMULATION DETECTION AND AVOIDANCE

(75) Inventors: Aaron R. McCabe, Minneapolis, MN (US); Shibaji Shome, Minneapolis, MN (US); Yanting Dong, Shoreview, MN (US); Amy Jean Brisben, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 364 days.

(21) Appl. No.: 12/724,729

(22) Filed: Mar. 16, 2010

(65) Prior Publication Data

US 2010/0262204 A1 Oct. 14, 2010

Related U.S. Application Data

(60) Provisional application No. 61/168,703, filed on Apr. 13, 2009.

(51) Int. Cl.
*A61N 1/39* (2006.01)

(52) U.S. Cl. .......................................... 607/9

(58) Field of Classification Search .......... 607/4–5, 607/9, 27–28
See application file for complete search history.

(56) References Cited

U.S. PATENT DOCUMENTS

| | | |
|---|---|---|
| 6,221,011 B1 | 4/2001 | Bardy |
| 6,270,457 B1 | 8/2001 | Bardy |
| 6,277,072 B1 | 8/2001 | Bardy |
| 6,280,380 B1 | 8/2001 | Bardy |
| 6,312,378 B1 | 11/2001 | Bardy |
| 6,336,903 B1 | 1/2002 | Bardy |
| 6,358,203 B2 | 3/2002 | Bardy |
| 6,368,284 B1 | 4/2002 | Bardy |
| 6,398,728 B1 | 6/2002 | Bardy |
| 6,440,066 B1 | 8/2002 | Bardy |
| 6,611,712 B2 | 8/2003 | Spinelli |
| 6,687,545 B1 * | 2/2004 | Lu .................................. 607/28 |
| 6,772,008 B2 | 8/2004 | Zhu |
| 6,915,163 B2 | 7/2005 | Spinelli |
| 6,937,901 B2 | 8/2005 | Zhu et al. |
| 6,978,178 B2 | 12/2005 | Sommer |
| 7,123,960 B2 | 10/2006 | Ding |
| 7,257,444 B2 | 8/2007 | Spinelli |

(Continued)

FOREIGN PATENT DOCUMENTS

| | | |
|---|---|---|
| EP | 1249254 | 10/2002 |
| EP | 2103327 | 9/2009 |

(Continued)

OTHER PUBLICATIONS

Jul. 1, 2010, International Search Report and Written Opinion from PCT Application No. PCT/US2010/030738, 19 pages.

(Continued)

*Primary Examiner* — Scott Getzow
*Assistant Examiner* — Amanda Patton
(74) *Attorney, Agent, or Firm* — Brooks, Cameron & Huebsch, PLL

(57) ABSTRACT

Cardiac resynchronization therapy is delivered to a heart using an extended bipolar electrode configuration in accordance with programmed pacing parameters including a non-zero intraventricular delay. The extended bipolar electrode configuration comprises a left ventricular electrode defining a cathode of the extended bipolar electrode configuration and a right ventricular electrode defining an anode of the extended bipolar electrode configuration. A pace pulse is delivered to the left ventricular electrode and anodal stimulation of the right ventricle is detected based on the sensed response to the pace pulse.

28 Claims, 11 Drawing Sheets

U.S. PATENT DOCUMENTS

| | | |
|---|---|---|
| 7,373,202 B1 | 5/2008 | Kroll |
| 2002/0151934 A1 | 10/2002 | Levine |
| 2007/0276446 A1 | 11/2007 | Spinelli |
| 2008/0287855 A1 | 11/2008 | Mower et al. |
| 2008/0319496 A1 | 12/2008 | Zhu et al. |
| 2009/0005830 A1 | 1/2009 | Zhu et al. |
| 2009/0030470 A1 | 1/2009 | Holmstrom |
| 2009/0043351 A1 | 2/2009 | Sathaye |
| 2009/0043352 A1 | 2/2009 | Brooke |

FOREIGN PATENT DOCUMENTS

| | | |
|---|---|---|
| WO | WO2006105474 | 10/2006 |
| WO | WO2007086782 | 8/2007 |
| WO | WO2009006331 | 1/2009 |

OTHER PUBLICATIONS

Van Gelder et al., "Changes in morphology of the paced QRS complex related to pacemaker output", Pacing Clin Electrophysio, 1989 12(10), p. 1640-1649 (abstract only).

Bulava et al., "Triple-site pacing in patients with biventricular device-incidence of the phenomenon and cardiac resynchronization benefit", J. Intev Card Electropyhsiol, 2004, 10(1), p. 37-45 (abstract only).

Meine et al., "Anodal stimulation in three chamber implantable cardioverter/defibrillator (ICD) devices with unipolar left ventricular pacing leads: Is it a problem for VV sequential pacing?", Europace, 2004, vol. 6(Supp. 1), p. 183.

Thibault et al., "Anodal right ventricular capture during left ventricular stimulation in CRT-implantable cardioverter defibrillators", Pacling Clin Electrophysiol, 2005, vol. 28(7), p. 613-619 (abstract only).

Steinhaus et al., "Anodal stimulation: A potential concern with biventricular pacing?", Pacing Clin Electrophysiol, 2001, vol. 24, p. 553 (no copy).

Van Gelder et al., right ventricular anodal capture during left ventricular stimulationin CRT-implantable cardioverter defibrillators (ICD), Pacing Clin Electrophysiol., 2006, vol. 29(3), p. 337 (no copy).

\* cited by examiner

Without Anodal Stimulation

With Anodal Stimulation

ANODAL STIMULATION DETECTION AND AVOIDANCE

RELATED APPLICATIONS

This application claims the benefit of Provisional Patent Application Ser. No. 61/168,703, filed on Apr. 13, 2009, to which priority is claimed pursuant to 35 U.S.C. §119(e) and which is hereby incorporated herein by reference.

FIELD OF THE INVENTION

The present invention relates generally to cardiac pacing therapy, and more specifically, to methods and systems for detecting anodal stimulation and mitigating same to provide enhanced cardiac resynchronization therapy.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

Cardiac arrhythmia occurs when the heart rhythm is irregular or if the heart rate is too slow or too fast. During an arrhythmic episode, the heart's pumping action may become impaired and blood flow to peripheral tissues may be inadequate. Cardiac arrhythmias have a number of etiological sources, including tissue damage due to myocardial infarction, infection, or degradation of the heart's ability to generate or synchronize the electrical impulses that coordinate contractions. Bradyarrhythmia occurs when the heart rhythm is too slow. This condition may be caused, for example, by impaired function of the SA node, denoted sick sinus syndrome, or by delayed propagation or blockage of the electrical impulse between the atria and ventricles. Bradyarrhythmia produces a heart rate that is too slow to maintain adequate circulation. Tachyarrhythmia occurs when the heart rate is too rapid. Tachyarrhythmia may have its origin in either the atria or the ventricles. Tachyarrhythmia occurring in the atria of the heart, for example, includes atrial fibrillation and atrial flutter. Both conditions are characterized by rapid contractions of the atria. In addition to being hemodynamically inefficient, the rapid contractions of the atria may also adversely affect the ventricular rate.

Ventricular tachyarrhythmia occurs when electrical activity arises in the ventricular myocardium at a rate more rapid than the normal sinus rhythm. Ventricular tachyarrhythmia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management (CRM) systems have been used as an effective treatment for patients with serious arrhythmias. CRM system operate by delivering relatively high energy electrical shocks to the heart to terminate tachyarrhythmia and/or by delivering relatively low energy electrical pulses to one or more heart chambers, causing the heart chambers to contract at heart rate that is hemodynamically sufficient.

Pacing therapy has also been used to improve cardiac output for patients who suffer from heart failure. Heart failure is frequently related to intraventricular and/or intraventricular conduction defects, e.g., bundle branch blocks which lead to cardiac dyssynchrony and reduced pumping action. To treat heart failure, CRM systems deliver timed pace pulses that produce more coordinated contractions of the atria and/or ventricles. The pace pulses are delivered to the heart chambers at specific intervals to achieve optimal improvement in pumping efficiency and cardiac output. Cardiac resynchronization pacing may include pacing both ventricles after a specified atrioventricular delay. The ventricular paces may be delivered simultaneously or separated by a programmable offset.

SUMMARY OF THE INVENTION

The present invention is directed to detecting anodal stimulation of a ventricle. Particular embodiments of the invention are directed to detecting anodal stimulation of a right ventricle when pacing the left ventricle and ameliorating undesirable anodal stimulation of the right ventricle.

According to various embodiments, a cardiac rhythm management system includes an implantable lead system comprising left and right ventricular electrodes configurable in at least an extended bipolar configuration and at least an alternative bipolar or unipolar configuration differing from the extended bipolar configuration. A left ventricular electrode defines a cathode of the extended bipolar configuration and a right ventricular electrode defines an anode of the extended bipolar configuration. Energy delivery circuitry and sensing circuitry are respectively coupled to the lead system. A controller is coupled to the sensing circuitry and the energy delivery circuitry. The controller is configured to execute program instructions for sensing cardiac electrical activity and delivering cardiac resynchronization therapy (CRT) to the heart in accordance with programmed pacing parameters including a non-zero intraventricular delay (IVD). The controller is configured to deliver a pace pulse to the left ventricular electrode defining the cathode of the extended bipolar configuration. A detector is coupled to the sensing circuitry and the controller. The detector is configured to sense for a response to the pace pulse and detect anodal stimulation of the right ventricle based on the sensed response.

The controller is configured to selectably switch from a current extended bipolar pace vector to an alternative bipolar or unipolar pace vector to mitigate or eliminate detected anodal stimulation of the right ventricle. The alternative pace vector is preferably a pacing vector that is different in configuration relative to the current extended bipolar pace vector, includes at least one left ventricular pace electrode, and may be an extended bipolar pace vector, an LV-only bipolar pace vector, or a unipolar or a bipolar pace vector comprising at least one LV electrode and one or more other cardiac electrodes, such as another lead electrode or a subcutaneous electrode (e.g., an active can electrode or indifferent electrode of the can). In various embodiments, the controller is configured to switch from the current extended bipolar pace vector to an alternative bipolar or unipolar pace vector that excludes the right ventricular electrode and includes at least one left ventricular electrode. According to some implementations, the controller is configured to selectably switch from a current extended bipolar pace vector to an alternative bipolar or unipolar pace vector without ganging an additional anode electrode with the right ventricular electrode to mitigate or eliminate detected anodal stimulation of the right ventricle.

In some embodiments, the anode of the current extended bipolar pace vector comprises a single right ventricular ring electrode, and the cathode of the current extended bipolar pace vector comprises at least one of a left ventricular ring electrode or a left ventricular tip electrode. In other embodiments, the lead system comprises a multiple-pole left ventricular lead comprising a multiplicity of left ventricular ring electrodes. At least one of the electrodes of the multiple-pole left ventricular lead defines the cathode of the current extended bipolar pace vector and the anode of the current extended bipolar pace vector comprises a single right ventricular ring electrode.

The controller may be configured to switch from a current extended bipolar pace vector to an alternative bipolar or unipolar pace vector that comprises at least one left ventricular pacing electrode. The controller may be configured to switch from the current extended bipolar pace vector to an alternative bipolar or unipolar pace vector comprising at least two left ventricular pacing electrodes. The controller may be configured to switch from the current extended bipolar pace vector to an alternative pace vector comprising an extended bipolar pacing electrode configuration differing from the current extended bipolar configuration and comprising at least one left ventricular pacing electrode. The controller may be configured to switch from the current extended bipolar pace vector to an alternative extended bipolar pace vector without ganging an additional anode electrode with the right ventricular electrode.

In accordance with other embodiments, methods of the invention involve selectably delivering cardiac resynchronization therapy (CRT) to a heart using at least an extended bipolar electrode configuration and at least an alternative bipolar or unipolar electrode configuration differing from the extended bipolar electrode configuration in accordance with programmed pacing parameters including a non-zero intraventricular delay (IVD). The extended bipolar electrode configuration comprises at least a left ventricular electrode defining a cathode of the extended bipolar electrode configuration and a right ventricular electrode defining an anode of the extended bipolar electrode configuration. Methods further involve delivering a pace pulse to the left ventricular electrode, sensing for a response to the pace pulse, and detecting anodal stimulation of the right ventricle based on the sensed response. Methods involve switching from a current extended bipolar pace vector to an alternative bipolar or unipolar pace vector to mitigate or eliminate detected anodal stimulation of the right ventricle. Representative method embodiments include those that involve switching from the current extended bipolar pace vector to an alternative unipolar pace vector that excludes the right ventricular electrode and includes at least one left ventricular electrode. According to some implementations, methods involve selectably switching from a current extended bipolar pace vector to an alternative bipolar or unipolar pace vector without ganging an additional anode electrode with the right ventricular electrode to mitigate or eliminate detected anodal stimulation of the right ventricle.

In some method embodiments, the anode of the current extended bipolar pace configuration comprises the single right ventricular ring electrode, the cathode of the current extended bipolar pace configuration comprises at least one left ventricular pace electrode, and the alternative bipolar or unipolar pace configuration comprises at least one left ventricular pace electrode. In other method embodiments, switching from the current extended bipolar pace vector to the alternative pace vector involve switching to an alternative extended bipolar pace vector differing from the current extended bipolar pace vector and comprising at least one left ventricular pace electrode. In further method embodiments, switching from the current extended bipolar pace vector to the alternative pace vector comprises switching to an alternative extended bipolar pace vector without ganging an additional anode electrode with the single right ventricular electrode.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
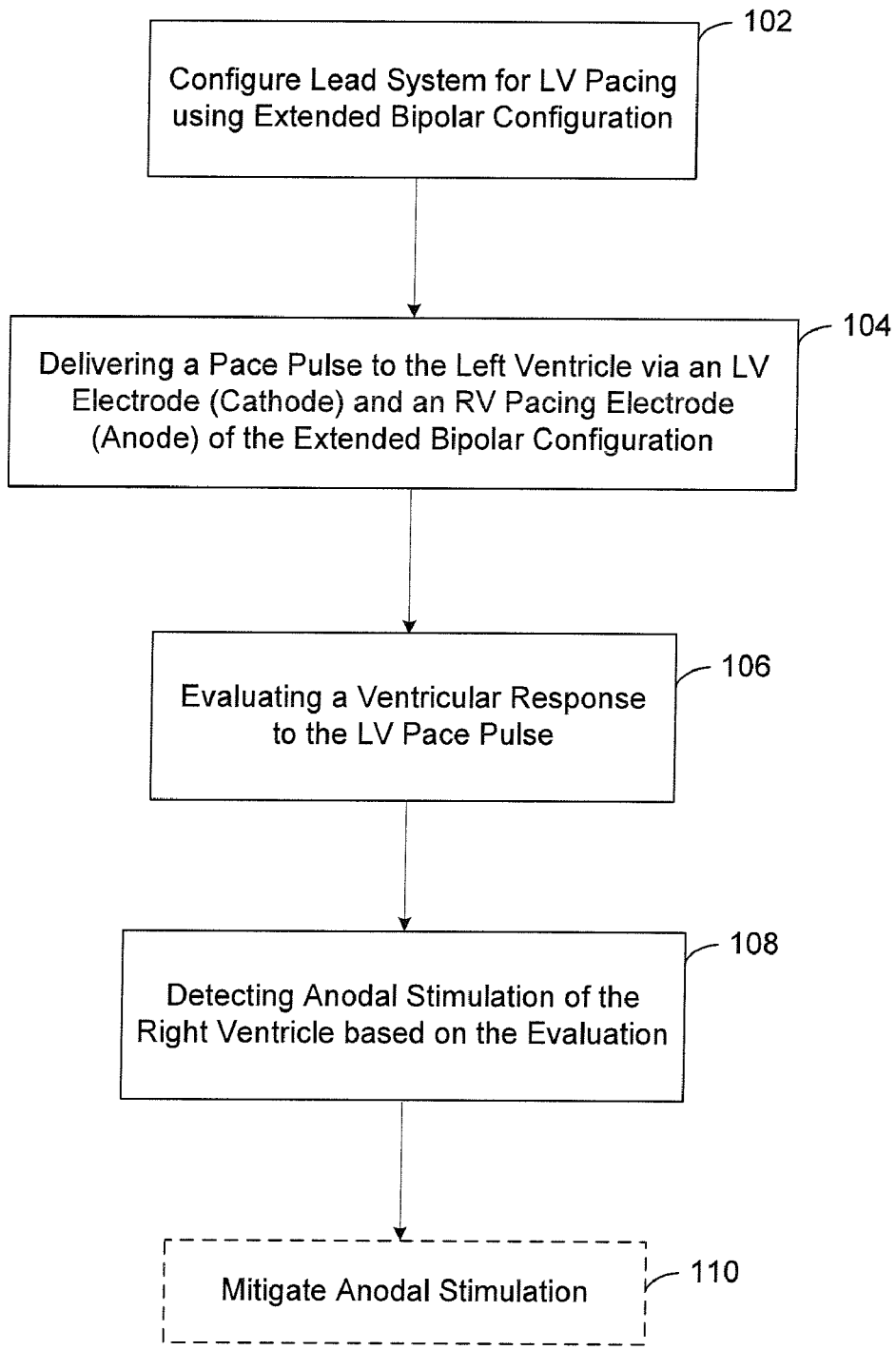
FIG. 1 is a flow diagram that illustrates a methodology for detecting anodal stimulation and mitigating same in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein below. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Mechanical contractions in the heart are triggered by waves of electrical depolarization that travel through the cardiac tissue. In a healthy heart, a depolarization wave for each cardiac cycle is initiated at the sinoatrial node and travels through the AV node, the His bundle, the left and right bundle branches and the Purkinje fibers to cause contractions of the ventricles. Due to age, disease, damage from myocardial infarction, and/or other degradation, the pathways and/or tissues involved in conduction of the depolarization wavefront may become compromised.

Pacemakers deliver electrical pace pulses to the heart to produce contractions of the heart chambers in synchrony and at a rate sufficient to meet the patient's metabolic demand. Pacing therapy involves the implementation of timing intervals between various events during a cardiac cycle. The timing intervals may be used to control the rate of heart chamber contractions and/or the synchrony between heart chamber contractions. For example, for patients whose intrinsic heart rate is too slow, pacing assists the heart in contracting at a rate that is sufficient to provide blood flow to meet the patient's metabolic requirements. For patients suffering from heart failure (HF), cardiac pacing may be used to ensure that the contractions of the heart chambers occur in a timed sequence that improves heart function.

Pacemakers typically include intracardiac electrodes arranged to be in electrical contact with the myocardium and configured to sense cardiac depolarization signals and/or deliver cardiac pace pulses in a timed sequence during cardiac cycles. For example, during a cardiac cycle, pacing escape intervals (pacing delays) may be established between a right or left atrial event and a right or left ventricular pace (AVD) and/or between a ventricular event in one chamber and a ventricular event in the opposite or contralateral chamber (intraventricular delay or IVD, also referred to as V-V delay). In applications having bi-atrial sensing and/or pacing capability, a pacing delay may be established between an atrial event in one chamber and an atrial event in the opposite chamber (IAD). One or more of the pacing delays may be adjusted to a predetermined value to enhance the pumping action of the heart. For example, in cardiac resynchronization pacing, the setting of the AVD and/or the IVD and/or the IAD can have a significant impact on hemodynamic function. These pacing escape intervals may be set to promote fusion between the left and right chamber depolarizations and/or to enhance ventricular preload.

Determining optimal pacing intervals, such as the AVD and/or IVD, may involve measurement of intrinsic conduction data while the patient is at rest or at a specified cardiac rate. Techniques for determining optimal pacing escape intervals are described in commonly owned U.S. Pat. No. 7,123,960, which is incorporated herein by reference in its entirety. These and other techniques that involve adjustment of the IVD, in particular, can be adversely impacted from undesirable effects of anodal stimulation. A variety of other processes typically performed by cardiac resynchronization therapy (CRT) and other CRM devices, such as capture verification, can also be adversely affected by undesirable effects of anodal stimulation.

Anodal stimulation is an unanticipated electrophysiologic phenomenon that can occur when pacing the heart using certain bipolar pacing configurations, such as an extended bipolar pacing configuration. An example of an extended bipolar pacing configuration is a lead system that incorporates a relatively small anode electrode in one chamber (typically the RV), like a typical RV bradycardia ring electrode. In some devices, such as ICDs, this can occur when the ICD electrode is a dedicated bipolar lead, since the extended bipolar paces to the RV ring (not the RV Coil), or in a true bradycardia configuration where there is no ICD lead present. Anodal stimulation can occur when pacing using other bipolar pacing output configurations, such as during LV bipolar pacing or RV bipolar pacing.

During pre-clinical studies involving left ventricular automatic capture threshold (LVAT) testing, it was noticed that, particularly during elevated pace amplitudes during a extended bipolar step-down voltage test, anodal stimulation can be problematic. Anodal stimulation can be problematic from a device algorithm standpoint as well as from a patient hemodynamic standpoint as it effectively negates any programmed IVD. For example, when the physician programs an IVD, it is expected that the programmed IVD will be the true delay between capture of the right and left ventricles. Anodal stimulation negates this expected delay between right and left ventricular capture.

Embodiments of the present invention are directed to detecting anodal stimulation of a ventricle. Various embodiments are directed to detecting anodal stimulation of a right ventricle when pacing the left ventricle. Embodiments of the present invention find particular utility for pacing regimens that utilize IVD timing that is non-zero. Various embodiments are directed to detecting anodal stimulation of a right ventricle when pacing the right and left ventricles with a programmed IVD. For example, embodiments are directed to single ventricular chamber pacing (e.g., left ventricular-only pacing, referred to herein as LV-only pacing) and detection of ventricular anodal stimulation (e.g., right ventricular (RV) anodal stimulation) by distinguishing between bi-ventricular capture (RV and LV capture) and single-ventricular capture (LV capture).

Embodiments of the present invention are directed to mitigating or eliminating anodal stimulation of a ventricle, such as anodal stimulation of a right ventricle when pacing the right and left ventricles with a programmed IVD. Various approaches to mitigating or eliminating anodal stimulation of a ventricle are contemplated, including modifying one or more pacing parameters and/or selecting (automatically or manually) one or more alternative pacing vectors. In some embodiments, an automatic vector selection algorithm may be implemented that evaluates IVD and left and/or right ventricular electrograms for anodal stimulation. Embodiments may be directed to alerting the patient's physician or reprogramming the pacing configuration (e.g., pacing parameters and/or pacing vector) to address detected anodal stimulation. Other inputs into an algorithm of the present invention that effects changes to pacing parameters and/or pacing vector to detect, mitigate, and/or eliminate anodal stimulation may include impedances, sense amplitudes, phrenic nerve stimulation thresholds, and capture thresholds, among others. Advantageously, no new sensing technology need be employed in accordance with various embodiments of the present invention.

Particular embodiments are directed to a cardiac resynchronization therapy system which includes an implantable lead system having left and right ventricular electrodes configurable in at least an extended bipolar configuration. In some configurations, a left ventricular electrode defines a cathode of the extended bipolar configuration and a right ventricular electrode defines an anode of the extended bipolar configuration. Energy delivery circuitry and sensing circuitry are respectively coupled to the lead system. A controller is coupled to the sensing circuitry and the energy delivery circuitry, and is configured to execute program instructions stored in memory for sensing cardiac electrical activity and delivering cardiac resynchronization therapy to the heart in accordance with programmed pacing parameters including a non-zero IVD. The controller is configured to deliver a pace pulse to the left ventricular electrode defining the cathode of the extended bipolar configuration. A detector is coupled to the sensing circuitry and the controller. The detector is configured to sense for a response to the pace pulse and detect anodal stimulation of the right ventricle based on the sensed response.

In some configurations, the anode of the extended bipolar configuration includes a right ventricular ring electrode and the cathode of the extended bipolar configuration comprises a left ventricular ring or tip electrode. In various configurations, the lead system includes a left ventricular lead having a number of the left ventricular electrodes that define a multiple-pole left ventricular lead. In such configurations, at least one of the electrodes of the multiple-pole left ventricular lead defines the cathode of the extended bipolar configuration. In other configurations, only one of the electrodes of the multiple-pole left ventricular lead defines the cathode of the extended bipolar configuration.

According to some embodiments, the detector may be configured to detect presence or absence of an expected right ventricular (RV) sense after a predetermined delay following delivery of the LV pace pulse, wherein presence of the expected RV sense detected after the predetermined delay is indicative of an absence of anodal stimulation of the right ventricle and non-detection of the expected RV sense after the predetermined delay is indicative of anodal stimulation of the right ventricle.

In various embodiments, memory of the implantable system is configured to store an expected evoked response template indicative of left ventricular capture responsive to left ventricular pacing using a bipolar or unipolar electrode configuration. The controller is configured to generate a second template indicative of left ventricular capture responsive to left ventricular pacing using the extended bipolar configuration, and the detector is configured to detect presence or absence of right ventricular anodal stimulation based on a comparison of the expected evoked response template and the second template.

In some embodiments, the detector is configured to detect right ventricular anodal stimulation during a right ventricular capture verification test. For example, the controller may be configured to deliver a predetermined number of left ventricular pace pulses using the extended bipolar configuration and the detector may be configured to detect a number of right ventricular capture events responsive to the predetermined number of left ventricular pace pulses. The detector may be configured to detect right ventricular anodal stimulation based on a comparison of the number of right ventricular capture events relative to the predetermined number of left ventricular pace pulses.

In accordance with various embodiments, the detector is configured to detect right ventricular anodal stimulation during a left ventricular capture threshold test. For example, the controller may be configured to implement a left ventricular capture threshold test using the extended bipolar configuration. The detector may be configured to detect LV capture and right ventricular anodal stimulation during the LV capture threshold test and determine an LV capture threshold value and an RV anodal stimulation threshold value. The detector may be configured to detect RV anodal stimulation resulting from an LV test pace based on a comparison of an LV evoked response (ER) template developed from ventricular responses to a predetermined number of LV paces during extended bipolar pacing relative to an expected LV ER morphological template developed from ventricular responses to a predetermined number of LV paces during bipolar or unipolar pacing. In some embodiments, the detector may be configured to detect fusion or non-capture based on a comparison of an LV evoked response template developed from LV responses to a predetermined number of LV paces that do not result in right ventricular anodal stimulation, such as bipolar or unipolar pacing, and a second LV ER template developed from ventricular responses to a predetermined number of LV paces that result in right ventricular anodal stimulation.

According to some embodiments, the controller may be configured to implement a left ventricular capture threshold test using the extended bipolar configuration. The detector may be configured to detect LV capture, RV anodal stimulation, and fusion/non-capture during the LV capture threshold test and determine an LV capture threshold value and an RV anodal stimulation threshold value.

In some embodiments, the controller may be configured to modify one or more left ventricular pacing parameters to mitigate or eliminate detected anodal stimulation of the right ventricle. In some embodiments, the controller may be configured to switch from a currently selected pacing vector to an alternative pacing vector to mitigate or eliminate detected anodal stimulation of the right ventricle.

Turning now to FIG. 1, there is shown a flow diagram that illustrates a methodology for detecting anodal stimulation in accordance with embodiments of the present invention. Some embodiments are directed to detecting anodal stimulation while others involve both detecting anodal stimulation and mitigating same. As is shown in FIG. 1, a lead system is configured 102 for left ventricular (LV) pacing using an extended bipolar electrode configuration. A pace pulse is delivered 104 to the left ventricle via an LV electrode acting as a cathode and an RV electrode acting as an anode of the extended bipolar configuration. A ventricular response to the LV pace pulse is evaluated 106. Sensing of the ventricular response may be effected using any available sensing vector. Anodal stimulation of the right ventricle is detected 108 based on the ventricular response evaluation. In some embodiments, processes are implemented 110 to mitigate or eliminate the anodal stimulation in the right ventricle.

Figure 2:
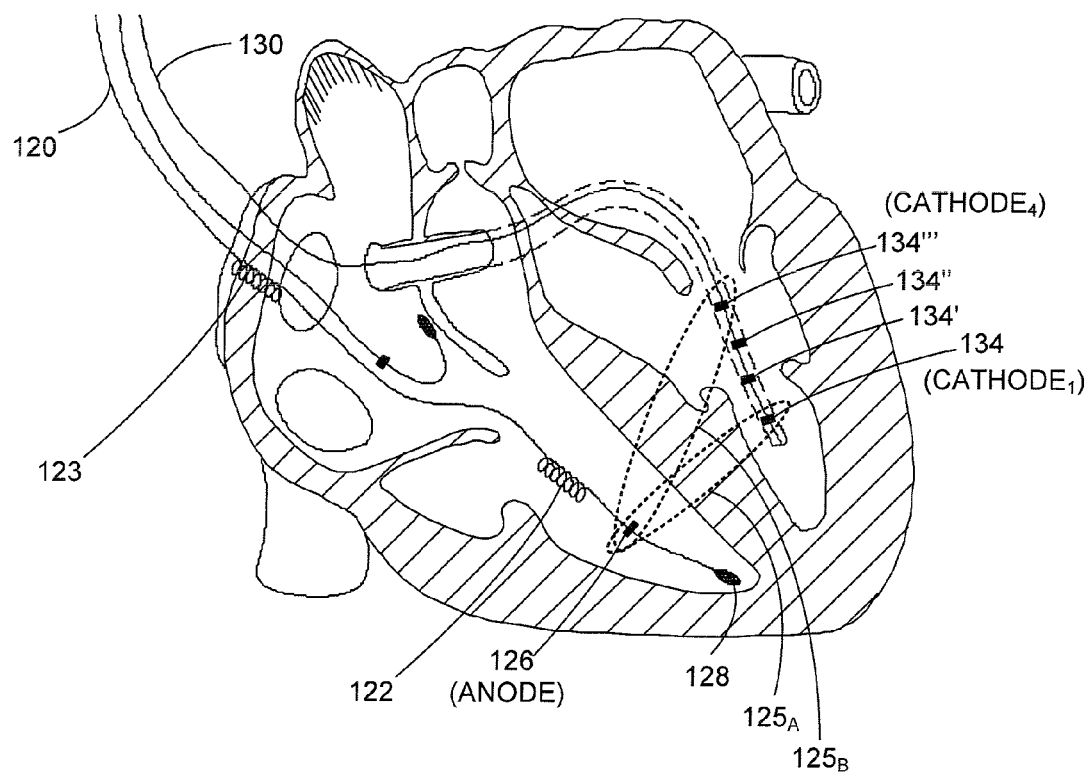
FIG. 2 illustrates a lead system implanted in a heart and having an extended bipolar configuration in accordance with embodiments of the present invention.

FIG. 2 illustrates a lead system implanted in a heart and having an extended bipolar configuration in accordance with embodiments of the present invention. The lead system in FIG. 2 includes a right atrial lead, a right ventricular lead, and a left ventricular lead. It is understood that other lead configurations are contemplated, including those with fewer or more leads, such as a left atrial lead. As is shown in FIG. 2, a left ventricular lead 130 includes a number of electrodes 134. Electrode 134 may be a tip electrode, but is preferably a distal ring electrode. Other electrodes 134', 134", and 134'" are ring electrodes disposed proximally of distal electrode 134.

A right ventricular lead 120 is also shown, which includes a distal electrode 128, that may be a tip electrode, and a proximal electrode 126, which may be a ring electrode 126. Other RV electrode configurations are contemplated. It is noted that lead configurations for CRT-P (pacing) devices would exclude defibrillation electrodes (e.g., electrode 122, electrode 123), while CRT-D (defibrillator) devices would include one or more defibrillation electrodes 122, 123. According to the embodiment shown in FIG. 2, an extended bipolar lead configuration is defined by one of the LV lead electrodes 134, 134', 134", 134'", acting as a cathode, and the ring electrode 126 of the RV lead, acting as an anode. For example, an extended bipolar lead configuration $125_A$ is defined by the distal electrode 134 (ring or tip) of the LV lead 130, acting as a cathode, and the ring electrode 126 of the RV lead, acting as an anode. By way of further example, an extended bipolar lead configuration $125_B$ is defined by a proximal ring electrode 134'" of the LV lead 130, acting as a cathode, and the ring electrode 126 of the RV lead, acting as an anode.

It will be appreciated that other ring electrodes of the LV lead, such as electrode 134' and 134", can be switchably selected to electrically cooperated with RV ring electrode 126 to form an extended bipolar lead configuration. It will be further appreciated that, in some embodiments, switching between cathode and anode electrodes to form different extended bipolar pacing lead configurations in the context of automatic vector selection embodiments of the present invention refers to selecting a single cathode electrode and a single anode electrode (e.g., only a sole RV tip electrode or only a sole RV ring electrode) so as to define an extended bipolar pacing cathode/anode electrode combination. It will be also appreciated that, in other embodiments, switching between cathode and anode electrodes to form different extended bipolar pacing lead configurations in the context of automatic vector selection embodiments of the present invention refers to selecting multiple cathode electrodes and a single anode electrode (e.g., only a sole RV tip electrode or only a sole RV ring electrode) so as to define an extended pacing bipolar cathode/anode electrode combination.

In general, preserving the benefits of extended bipolar pacing is achieved by selecting, automatically or semi-manually, a pacing configuration that includes one or more cathode electrodes in the left ventricle (or in the coronary sinus or left ventricular coronary vein) and a single right ventricular anode electrode. For example, ganging together one or more other anode electrodes (e.g., can electrode, indifferent electrode, right heart coil electrode, coronary sinus coil electrode) with a right ventricular anodic electrode (e.g., RV ring) is not generally advisable for achieving beneficial extended bipolar pacing in contra-lateral ventricular chambers.

According to one representative approach, a controller of a CRM device is configured to switch from a currently selected extended bipolar pace vector to an alternative bipolar or unipolar pace vector (extended or non-extended) without ganging an additional anode electrode with the right ventricular electrode to mitigate or eliminate detected anodal stimulation of the right ventricle. According to another representative approach, a controller of a CRM device is configured to switch from a currently selected extended bipolar pace vector to the alternative bipolar or unipolar pace vector that changes the left ventricular pacing vector (by selecting a different LV electrode or selecting a different combination of LV electrodes that may or may not include a previously selected LV electrode and may or may not include an RV electrode) without ganging an additional anode electrode with the right ventricular electrode to mitigate or eliminate detected anodal stimulation of the right ventricle. In other representative approaches, a controller of a CRM device is configured to switch from a currently selected extended bipolar pace vector to an alternative unipolar pace vector that includes at least one LV electrode and a subcutaneous or can electrode (active can electrode or indifferent electrode on the can) without ganging an additional anode electrode with the right ventricular electrode to mitigate or eliminate detected anodal stimulation of the right ventricle.

Figure 3A:
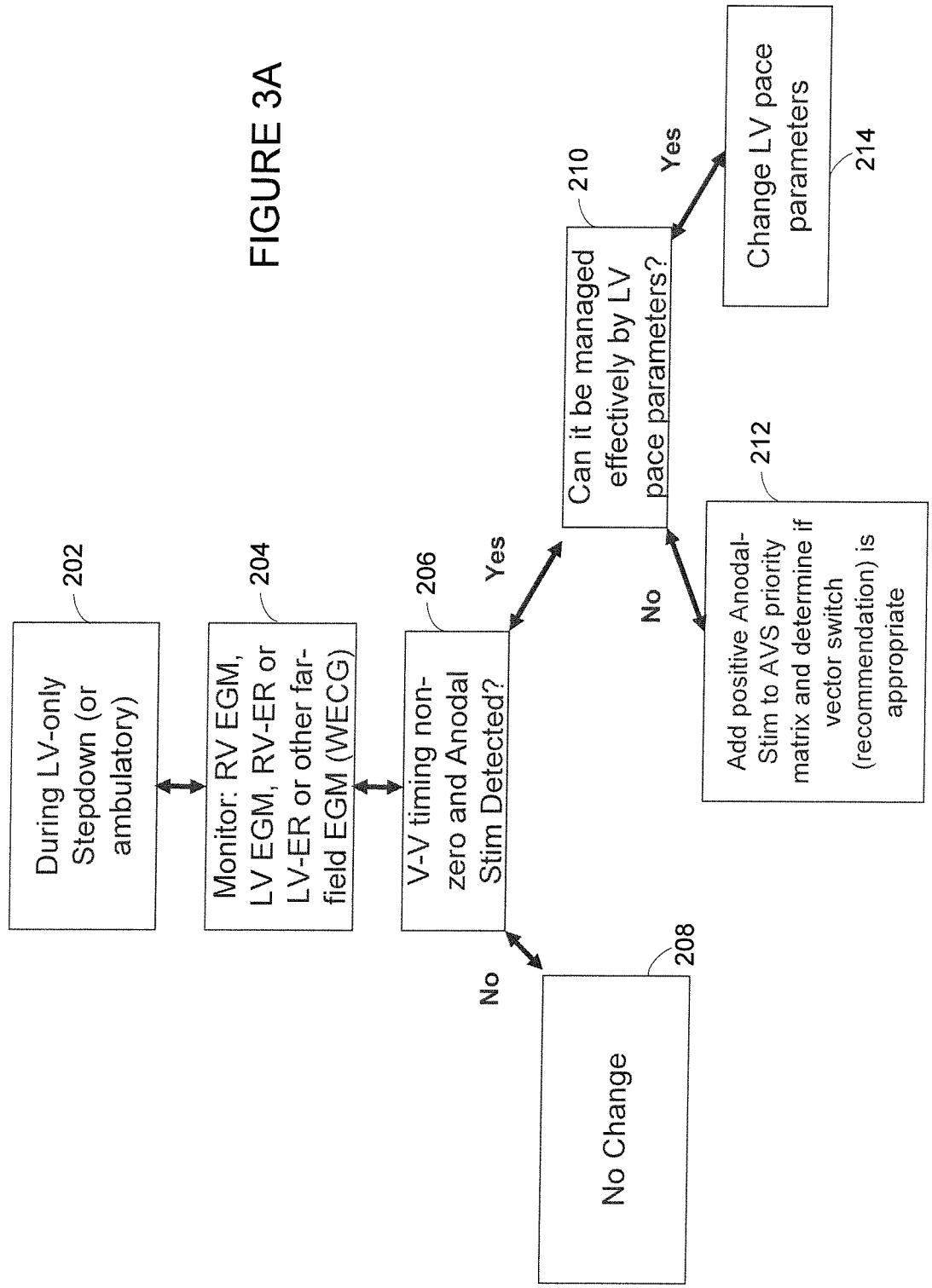
FIG. 3A is a flow diagram that illustrates a methodology for detecting anodal stimulation and mitigating same in accordance with embodiments of the present invention.

FIG. 3A is a flow diagram that illustrates a methodology for detecting anodal stimulation and mitigating same in accordance with embodiments of the present invention. In FIG. 3A, various processes are shown that can be performed during a clinician-initiated LV-only stepdown test (e.g., capture threshold test) or automatically during ambulatory operation 202 of the CRM device. During LV-only stepdown testing or ambulatory operation, various cardiac signals may be acquired by the CRM device. Such monitoring 204 may include monitoring of one or more of the RV EGM channel, LV EGM channel, RV-ER channel, LV-ER channel, or other far-field EGM channel, such as a wide or leadless ECG (WECG) channel.

If the IVD is non-zero, either by programming or via automatic device adjustment, and anodal stimulation of the right ventricle is detected 206 by evaluating one or more characteristics of at least one of the cardiac signals shown in Block 204, then a check is made to determine if RV anodal stimulation can be managed 210 by modifying LV pace parameters, such as pulse amplitude or width. If so, LV pace parameters are changed 214 to mitigate or eliminate the RV anodal stimulation. If LV pace parameter adjustment does not mitigate or eliminate the RV anodal stimulation, the pacing vector is preferably changed 212 to an alternative pacing vector. Suitable alternative pacing vectors include various bipolar and unipolar pacing vectors, including extended bipolar pacing vectors. Changing 212 to the alternative pacing vector may involve selecting different LV electrode(s) to define a bipolar or unipolar pace vector or selecting a different extended bipolar pace vector. Testing can be performed to determine if the change in pacing vector results in mitigation or elimination of the RV anodal stimulation.

In accordance with embodiments that employ an automatic vector selection (AVS) capability, detection of anodal stimulation that cannot be mitigated or eliminated by a change in pacing parameters results in the addition 212 of "positive anodal stimulation" to an AVS priority matrix. The AVS priority matrix is used by the AVS algorithm during prioritized selection of alternative pacing vectors. Embodiments of a CRM device that employs AVS and which can be implemented to include anodal stimulation detection and/or mitigation/elimination is described in commonly owned U.S. Published Patent Application Nos. 2009/0043351 and 2009/0043352, each of which is incorporated herein by reference in its entirety.

A determination is made 212 whether a pacing vector switch (actual switching operation or a recommendation) is appropriate. If deemed appropriate, an alternative pacing vector may be selected and either switched or recommended for switching to the physician. As is tested in Block 206, if either the IVD is not non-zero 206 or anodal stimulation is not detected 206, then no changes are made to the LV pacing parameters or vectors.

Figure 3B:
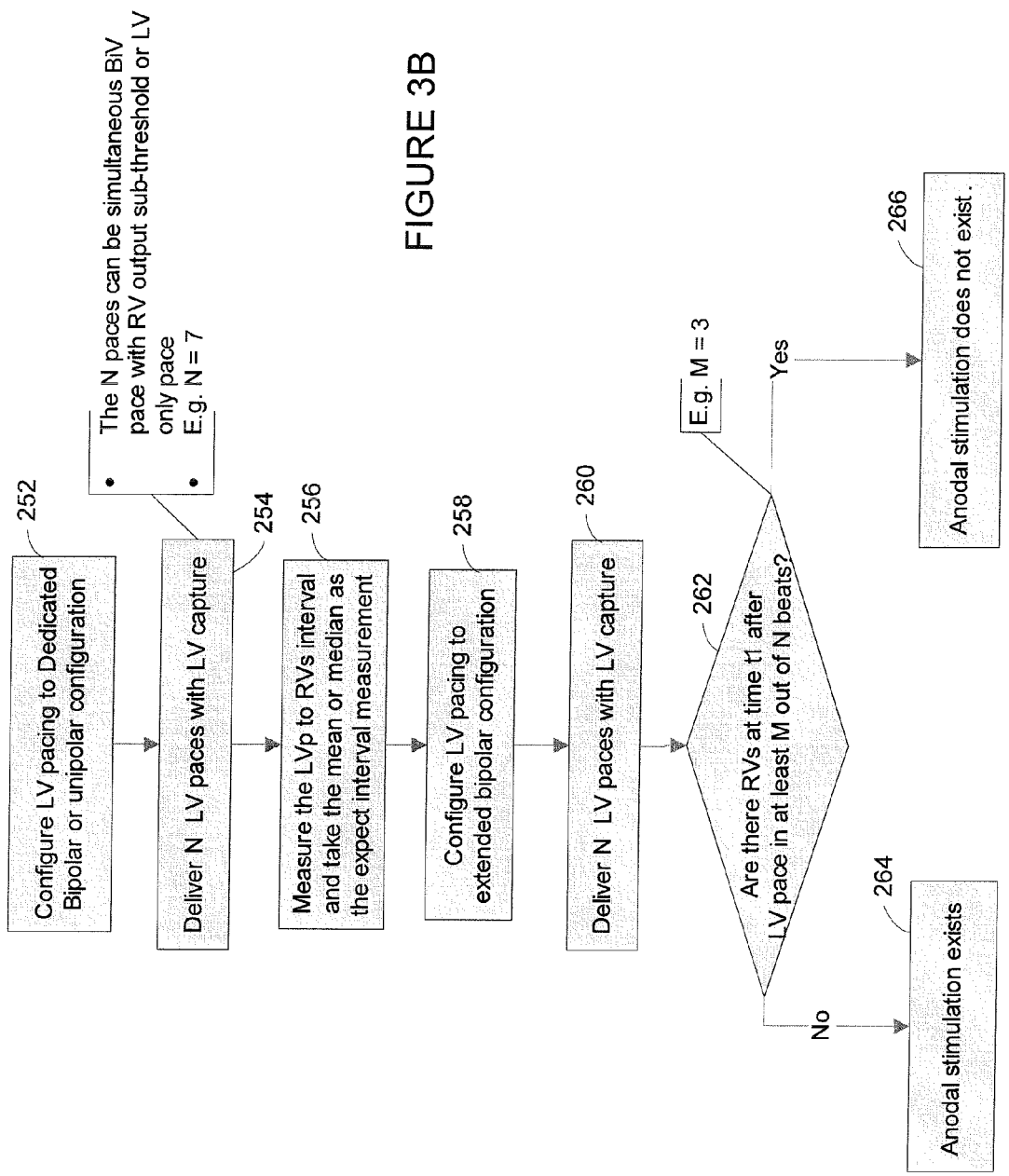
FIG. 3B is a flow diagram that illustrates a methodology for detecting anodal stimulation using a timing interval based approach in accordance with embodiments of the present invention.

FIG. 3B is a flow diagram that illustrates a methodology for detecting RV anodal stimulation using a timing interval based approach in accordance with embodiments of the present invention. In FIG. 3B, the CRM device is configured to implement 252 LV-only pacing using a dedicated bipolar or unipolar configuration. A predetermined number, N (e.g., N=7), of LV pace pulses are delivered 254 that achieve LV capture. The predetermined number of LV pace pulses may be simultaneous bi-ventricular paces with RV output sub-threshold or LV-only paces. A time interval, $t_1$, defined between the LV pace and RV sense is measured 256 for each of the N LV paces, and a mean or median of these intervals is computed as an expected $LV_P$-to-$RV_S$ interval ($t_1$) measurement.

The pacing vector is changed 258 from LV pacing using a dedicated bipolar or unipolar configuration to LV pacing using an extended bipolar configuration. A predetermined number of LV pace pulses are delivered 260 that achieve LV capture 260. The number of RV senses that are detected substantially at time $t_1$ following each of the N LV paces is determined. If at least a predetermined number, M (e.g., M=3), of the RV senses out of N (e.g., N=7) LV paces is detected 262, then anodal stimulation in the right ventricle is deemed 266 not to be present. If less than a predetermined number, M, of the RV senses out of N LV paces is not detected 262, then anodal stimulation in the right ventricle is deemed 264 to be present.

Figure 4A:
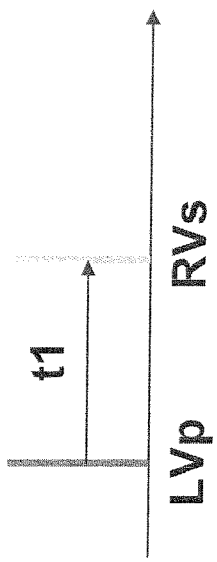
FIG. 4A shows a timing relationship between a left ventricular pace and a right ventricular sense in the absence of anodal stimulation.
Figure 4B:
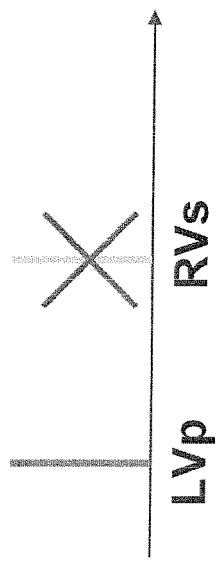
FIG. 4B shows an absence of a right ventricular sense after delivery of a left ventricular pace due to anodal stimulation.

FIG. 4A shows a timing relationship between an LV pace and an RV sense in the absence of anodal stimulation. In this case, a time interval, $t_1$, is defined between the LV pace and the RV sense. An expected time delay, $t_1$, thus occurs between the LV pace and the RV sense when anodal stimulation of the RV does not occur. In FIG. 4B, it is understood that the RV activity that is depicted as "missing" by an "X" is actually coinciding with the LV pace (i.e., is not purposefully delayed). FIG. 4B shows an absence of an RV sense and, therefore, time delay $t_1$, following delivery of an LV pace due to anodal stimulation of the right ventricle.

Figure 5:
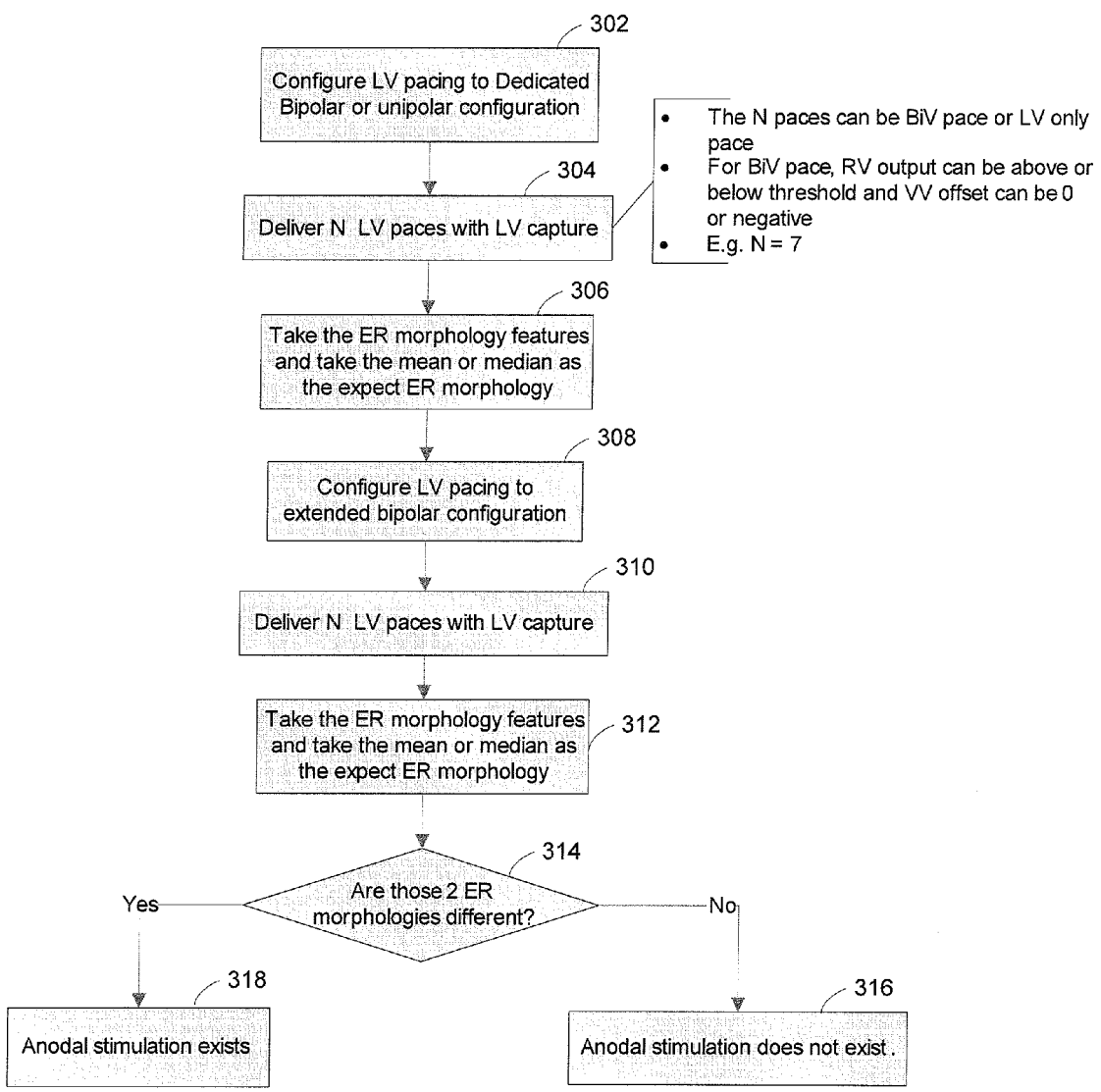
FIG. 5 is a flow diagram that illustrates a methodology for detecting anodal stimulation using an evoked response morphology based approach in accordance with embodiments of the present invention.

FIG. 5 is a flow diagram that illustrates a methodology for detecting anodal stimulation using an evoked response morphology based approach in accordance with embodiments of the present invention. As shown in FIG. 5, pacing by the CRM device is configured 302 to LV-only pacing using a dedicated bipolar or unipolar configuration. A predetermined number, N, of LV pace pulses are delivered 304 that achieve LV capture. The predetermined number of LV pace pulses may be bi-ventricular paces or LV-only paces. In the case of bi-ventricular paces, the RV output can be above or below threshold and the IVD can be zero or negative. Ventricular responses to the N LV paces are sensed using any desired sense vector. In particular, features of the evoked response (ER) for each of the N LV paces are detected and stored, and the mean or median of theses features is computed, from which an expected ER morphological template is generated 306.

The CRM device is configured 308 from LV-only pacing using a dedicated bipolar or unipolar configuration to LV pacing using an extended bipolar configuration. A predetermined number, N, of LV pace pulses are delivered 310 that achieve LV capture. An evoked response is detected and stored for each LV pace pulse, and the mean or median of the features is computed, from which a second ER morphological template is generated 312. The second ER morphological template is compared to the expected ER morphological template 314. If the two ER templates differ 314 by a predetermined match criterion (e.g., a predetermined correlation coefficient threshold value), then anodal stimulation is deemed 318 to be present, otherwise it is deemed 316 not to be present.

Figure 6:
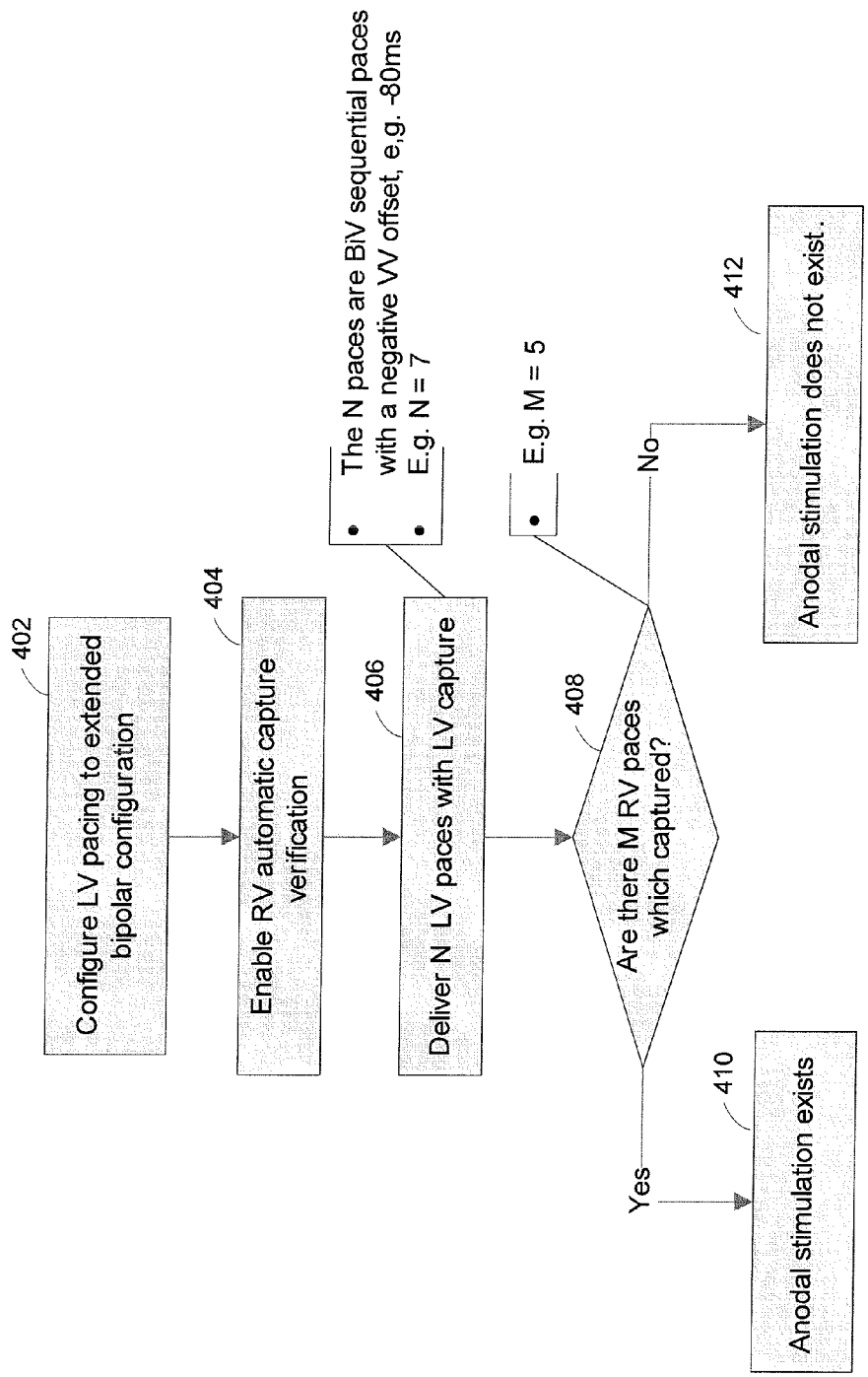
FIG. 6 is a flow diagram that illustrates a methodology for performing a right ventricular capture verification test that employs detection of anodal stimulation in accordance with embodiments of the present invention.

FIG. 6 is a flow diagram that illustrates a methodology for performing a right ventricular capture verification test that employs detection of anodal stimulation in accordance with embodiments of the present invention. The CRM device is configured 402 to LV pacing using an extended bipolar configuration. Automatic RV capture verification is enabled 404. A predetermined number, N, of LV pace pulses are delivered 406 that achieve LV capture. The predetermined number of LV pace pulses are preferably, but not necessarily, bi-ventricular sequential paces with a negative IVD (e.g., −80 ms). If there are a predetermined number, M, of RV paces that are detected captured, as tested in Block 408, then anodal stimulation is deemed 410 to be present, otherwise anodal stimulation is deemed not to be present 412.

Figure 7:
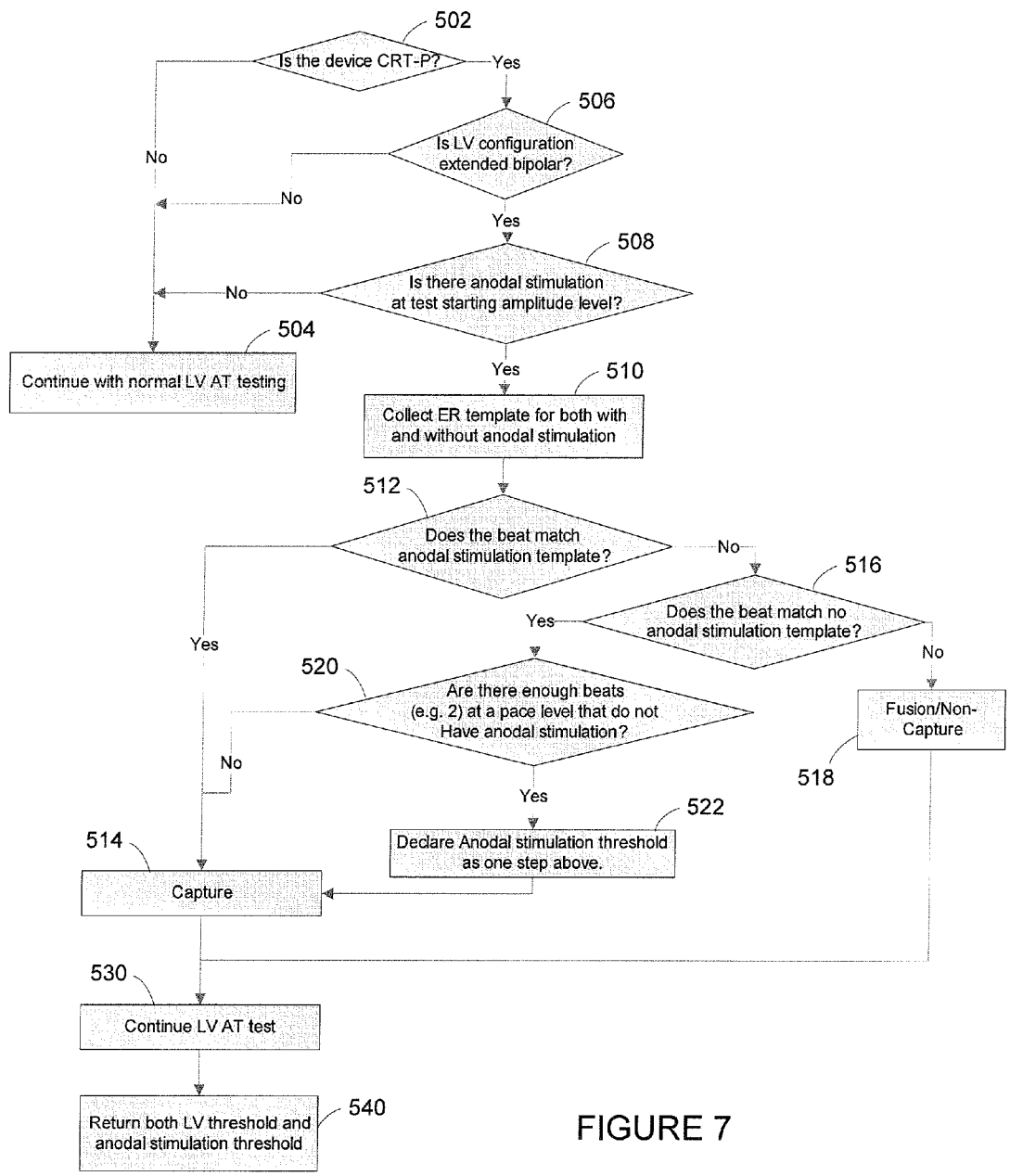
FIG. 7 is a flow diagram that illustrates a methodology for performing a left ventricular capture threshold test that employs detection of anodal stimulation in accordance with embodiments of the present invention.

FIG. 7 is a flow diagram that illustrates a methodology for performing a left ventricular capture threshold test, such as an automatic LV capture threshold (LVAT) test, that employs detection of anodal stimulation in accordance with embodiments of the present invention. If the CRM device is not a CRT-P device or is not operating in such a manner 502, then normal LVAT testing commences 504. If the CRM device is a CRT-P device, then a check is made 506 to determine if the pacing configuration is an extended LV bipolar electrode configuration. If not, then normal LVAT testing commences or continues 504.

If the pacing configuration is an extended LV bipolar electrode configuration, a check is made to determine if anodal stimulation 508 is present at the starting amplitude level of the capture threshold test. If so, a first ER template is generated or collected 510 for LV paces with anodal stimulation. A second ER template is generated or collected 510 for LV paces without anodal stimulation. If the beat responsive to the LV test pace pulse matches the first ER template (i.e., template for LV paces with anodal stimulation), then capture is detected 514. If the beat responsive to the LV test pace pulse does not match the first ER template, then a check is made to determine 516 if the beat matches the ER template when there is no anodal stimulation (i.e., the second ER template).

If the beat matches the second template (i.e., the template when anodal stimulation does not exist), then a check is made to determine 520 if there are enough beats (e.g., 2) at a pace amplitude level that do not have anodal stimulation. If so, an anodal stimulation threshold is declared 522 as one step above the current pace amplitude level. If not, then capture is detected 514. If the beat does not match either the first or the second template, as is tested at Block 516, then fusion or non-capture is detected 518. LVAT testing continues 530, and both the LV capture threshold and anodal stimulation threshold are returned 540.

Figure 8:
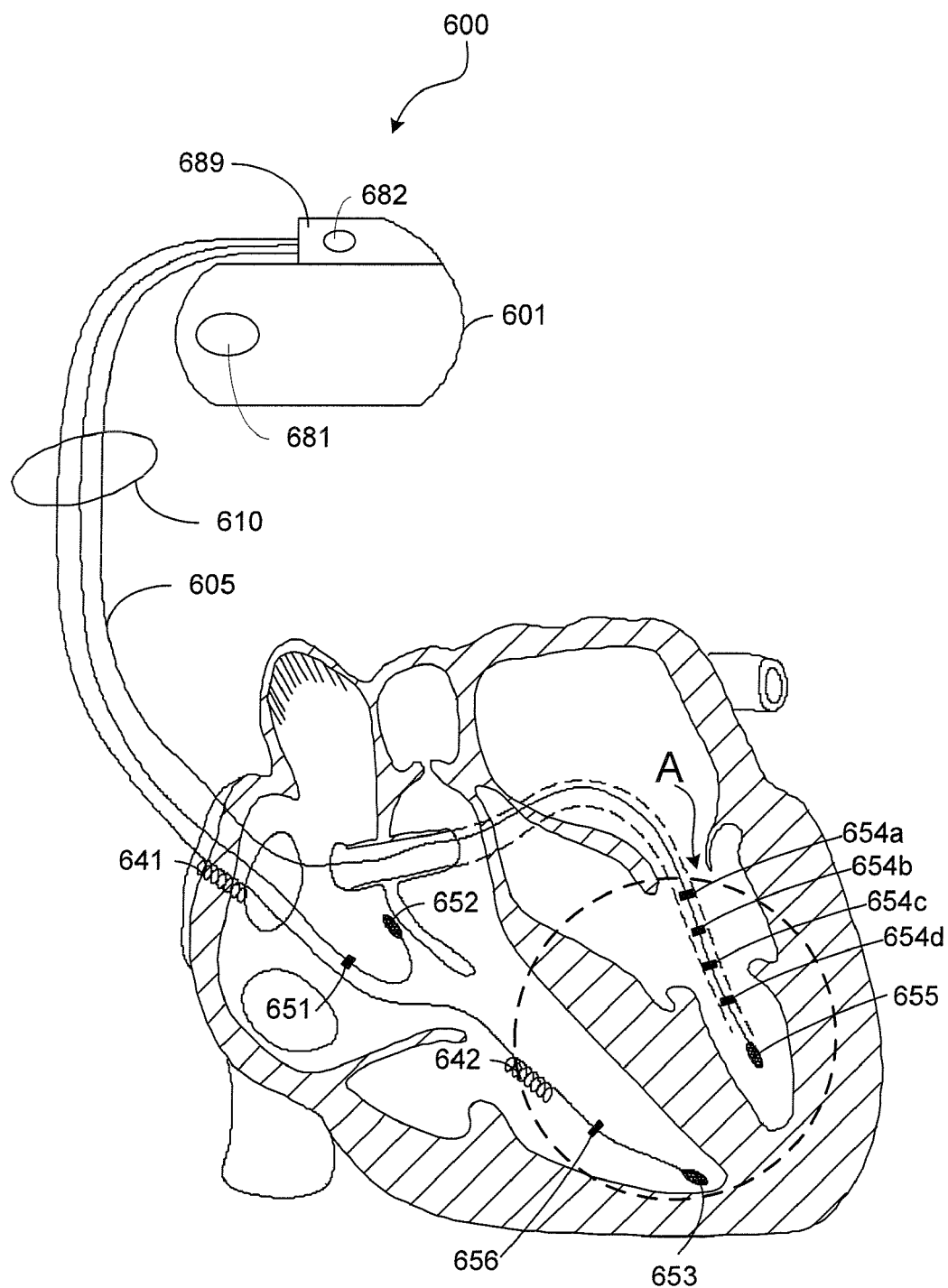
FIG. 8 shows an embodiment of a cardiac rhythm management device that may be used to deliver various therapies to the heart, and to detect and mitigate anodal stimulation in accordance with embodiments of the invention.

The therapy device 600 illustrated in FIG. 8 employs circuitry capable of implementing anodal stimulation techniques described herein, as well as electrode combination selection techniques for those embodiments that implement same. The therapy device 600 includes CRM circuitry enclosed within an implantable housing 601. The CRM circuitry is electrically coupled to an intracardiac lead system 610. Although an intracardiac lead system 610 is illustrated in FIG. 8, various other types of lead/electrode systems may additionally or alternatively be deployed. For example, the lead/electrode system may comprise and epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 610 are shown inserted into the patient's heart. The lead system 610 includes cardiac pace/sense electrodes 651-656 positioned in, on, or about one or more heart chambers for sensing electrical signals from the patient's heart and/or delivering pace pulses to the heart. The intracardiac sense/pace electrodes 651-656, such as those illustrated in FIG. 8, may be used to sense and/or pace one or more chambers of the heart, including the left ventricle, the right ventricle, the left atrium and/or the right atrium. The CRM circuitry controls the delivery of electrical stimulation pulses delivered via the electrodes 651-656. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes to support cardiac function consistent with a prescribed therapy. The lead system 610 includes defibrillation electrodes 641, 642 for delivering defibrillation/cardioversion pulses to the heart.

The left ventricular lead 605 incorporates multiple electrodes 654a-654d and 655 positioned at various locations within the coronary venous system proximate the left ventricle. Stimulating the ventricle at multiple locations in the left ventricle or at a single selected location may provide for increased cardiac output in a patients suffering from heart failure, for example, and/or may provide for other benefits. Electrical stimulation pulses may be delivered via the selected electrodes according to a timing sequence and output configuration that enhances cardiac function. Although FIG. 8 illustrates multiple left ventricle electrodes, in other configurations, multiple electrodes may alternatively or additionally be provided in one or more of the right atrium, left atrium, and right ventricle.

Portions of the housing 601 of the implantable device 600 may optionally serve as one or more multiple can 681 or indifferent 682 electrodes. The housing 601 is illustrated as incorporating a header 689 that may be configured to facilitate removable attachment between one or more leads and the housing 601. The housing 601 of the therapy device 600 may include one or more can electrodes 681. The header 689 of the therapy device 600 may include one or more indifferent electrodes 682. The can 681 and/or indifferent 682 electrodes may be used to deliver pacing and/or defibrillation stimulation to the heart and/or for sensing electrical cardiac signals of the heart.

Communications circuitry is disposed within the housing 601 for facilitating communication between the CRM circuitry and a patient-external device, such as an external programmer or advanced patient management (APM) system. The therapy device 600 may also include sensors and appropriate circuitry for sensing a patient's metabolic need and adjusting the pace pulses delivered to the heart and/or updating the electrode combination selection to accommodate the patient's metabolic need.

In some implementations, an APM system may be used to perform some of the processes discussed here, including evaluating, estimating, comparing, ordering, selecting, and updating, among others. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference in each of their respective entireties.

In certain embodiments, the therapy device 600 may include circuitry for detecting and treating cardiac tachyarrhythmia via defibrillation therapy and/or anti-tachyarrhythmia pacing (ATP). Configurations providing defibrillation capability may make use of defibrillation coils 641, 642 for delivering high energy pulses to the heart to terminate or mitigate tachyarrhythmia.

CRM devices using multiple electrodes, such as illustrated herein, are capable of delivering pace pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pace pulses between selected electrode combinations within a heart chamber during different cardiac cycles.

Figure 9:
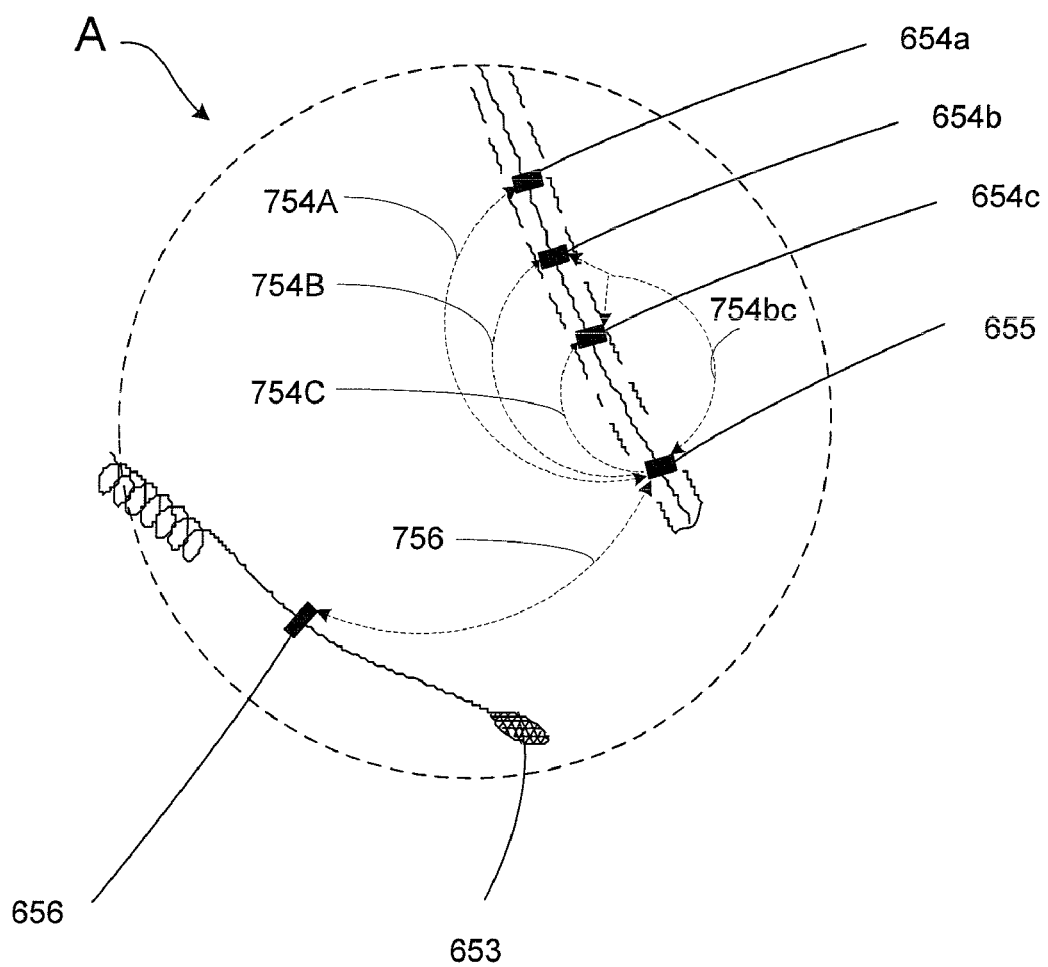
FIG. 9 shows an exploded view of Region A shown in FIG. 8, and illustrates a multiple-pole left ventricular lead and various pacing electrode combinations that may be selected for enhancing cardiac resynchronization therapy and mitigating anodal stimulation in accordance with embodiments of the invention.

FIG. 9 illustrates an enlarged view of the Region A delineated by the dashed line circle in FIG. 8. FIG. 9 illustrates various pacing configurations 754a, 754b, 754c, 754d, 754cd, and 756 that may be used to deliver pace pulses. Each of the pacing configurations 754a, 754b, 754c, 754d, 754cd, and 756 includes a common cathode electrode 655 (which is shown as a tip electrode for purposes of illustration, but could also be a distal ring electrode). Pacing configuration 754a is defined between cathode electrode 655 and anode electrode 654a; pacing configuration 754b is defined between cathode electrode 655 and anode electrode 654b; pacing configuration 754c is defined between cathode electrode 655 and anode electrode 654c; pacing configuration 754d is defined between cathode electrode 655 and anode electrode 654d; pacing configuration 756 is defined between cathode electrode 655 and anode electrode 656. An extended bipolar configuration is defined between cathode electrode 655 positioned in the left ventricle and anode electrode 656 positioned in the right ventricle. In some configurations, the pacing configuration cathode, or the pacing configuration anode, or both, may comprise multiple electrodes. For example, pacing configuration 754cd includes cathode electrode 655 and anode electrodes 654c and 654d.

Each of the pacing configurations discussed above correspond to an electrode combination, and each pacing configuration and electrode combination likewise correspond to a pacing site and/or vector. Delivering an identical electrical therapy using each electrode combination can elicit a different response from the patient. For example, therapy delivered at one electrode combination may be more likely to capture a chamber than another site. Also, therapy delivered using one electrode combination may be more likely to stimulate the diaphragm than another site. By way of further example, therapy delivered at one electrode combination may encourage anodal stimulation while delivery of the same therapy at a different electrode combination may discourage anodal stimulation.

Therefore, it is important to identify the electrode combination through which optimum therapy can be delivered, such as those that mitigate or eliminate anodal stimulation. In some cases, the optimum electrode combination for therapy is one that causes the desired response, using the smallest amount of power (such as battery storage), that does not cause undesirable stimulation. For example, an optimal electrode combination may be an electrode combination through which a delivered therapy captures the intended chamber requiring the smallest amount of voltage and current and one that does not produce anodal stimulation, stimulate the diaphragm or skeletal muscles, or other extra-cardiac tissue.

In multi-electrode pacing systems, multiple pacing electrodes may be disposed in a single heart chamber, in multiple heart chambers, and/or elsewhere in a patient's body. Electrodes used for delivery of pace pulses may include one or more cathode electrodes and one or more anode electrodes. Pace pulses are delivered via the cathode/anode electrode combinations, where the term "electrode combination" denotes that at least one cathode electrode and at least one anode electrode are used. An electrode combination may involve more than two electrodes, such as when multiple electrodes that are electrically connected are used as the anode and/or multiple electrodes that are electrically connected are used as the cathode.

Typically, pacing energy is delivered to the heart tissue via the cathode electrode(s) at one or more pacing sites, with a return path provided via the anode electrode(s). If capture occurs, the energy injected at the cathode electrode site creates a propagating wavefront of depolarization which may combine with other depolarization wavefronts to trigger a contraction of the cardiac muscle. The cathode and anode electrode combination that delivers the pacing energy defines the pacing vector used for pacing. The position of the cathode relative to cardiac tissue can be used to define an electrode combination and/or a pacing site.

Pace pulses may be applied through multiple electrodes (i.e., pacing vectors defined by various electrode combinations) in a single cardiac chamber in a timed sequence during the cardiac cycle to improve contractility and enhance the pumping action of the heart chamber. It is desirable for each pace pulse delivered via the multiple electrode combinations to capture the cardiac tissue proximate the cathode electrode while not producing undesirable anodal stimulation. The pacing energy required to capture the heart is dependent on the electrode combination used for pacing, and different electrode combinations can have different energy requirements for capture and different energies that can produce anodal stimulation. Particularly in the left ventricle, the minimum energy required for capture (capture threshold) without anodal stimulation may be highly dependent on the particular electrode combination used.

Pacing characteristics of therapy delivery using each electrode combination of a number of possible electrode combinations are dependent on many factors, including the distance between the electrodes, proximity to target tissue, type of tissue contacting and between the electrodes, impedance between the electrodes, resistance between the electrodes, and electrode type, among other factors. Such factors can influence the capture threshold and anodal stimulation threshold for the electrode combination, among other parameters. Pacing characteristics can vary with physiologic changes, electrode migration, physical activity level, body fluid chemistry, hydration, and disease state, among others. Therefore, the pacing characteristics for each electrode combination are unique, and some electrode combinations may work better than others for delivering a particular therapy that improves cardiac function consistent with a prescribed therapy.

In this way, electrode combination selection should take into consideration at least the efficacy of one or more electrode combinations of a number of electrodes in supporting cardiac function in accordance with a prescribed therapy. The efficacy of one or more electrode combinations of a number of electrodes in supporting cardiac function in accordance with a prescribed therapy can be evaluated by consideration of one or more parameters produced by electrical stimulation, such as capture threshold and anodal stimulation threshold.

Electrical stimulation delivered to one body structure to produce a desired therapeutic activation may undesirably cause activation of another body structure. For example, electrical cardiac pacing therapy can inadvertently stimulate bodily tissue, including nerves and muscles. Stimulation of extra-cardiac tissue, including phrenic nerves, the diaphragm, and skeletal muscles, can cause patient discomfort and interfere with bodily function.

A patient's evoked response from an electrical cardiac therapy can be unpredictable between electrode combinations. For example, an electrical cardiac therapy delivered using one electrode combination may produce an undesirable activation while an identical electrical cardiac therapy delivered using another electrode combination may not produce the undesirable activation.

As such, selecting an appropriate electrode combination, such as one electrode combination of a number of electrode combinations made possible by a multi-electrode lead that affects the desired cardiac response with the least amount of energy consumption and that does not unintentionally stimulate tissue, can be many-factored and complicated.

Manually testing each parameter of interest for each possible cathode-anode electrode combination can be a time consuming process for doctors, clinicians, and programmers. Furthermore, it can be difficult to sort through numerous different parameters for multiple pacing electrode combinations and understand the various tissue activation responses of electrical therapy delivered using various electrode combinations. Systems and methods of the present invention that employ LVAT testing with anodal stimulation detection can simplify these and other process.

Figure 10:
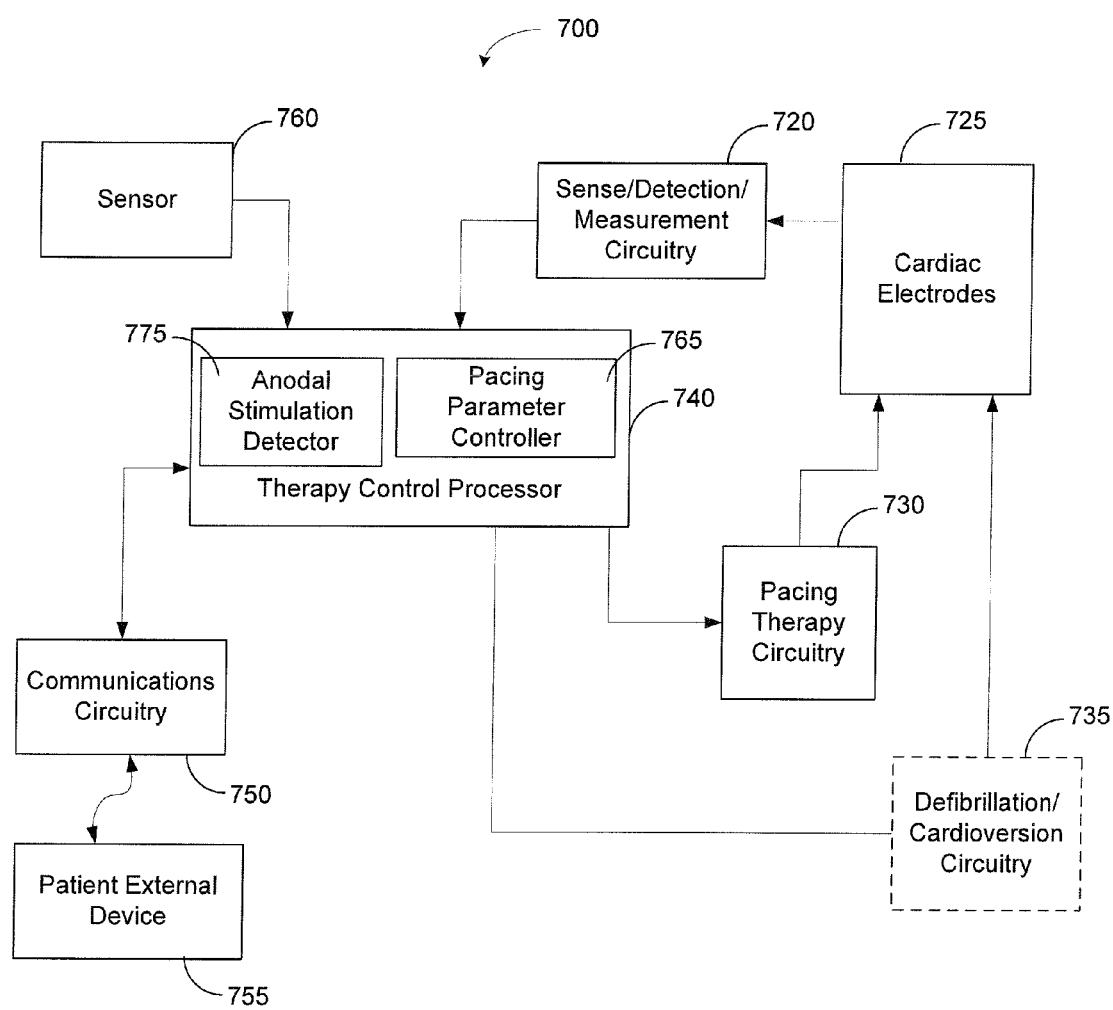
FIG. 10 is a block diagram of a system configured to implement program instructions stored in memory for delivering cardiac resynchronization therapy, and detecting and mitigating anodal stimulation in accordance with embodiments of the invention.

FIG. 10 is a block diagram depicting various components of a system that may be used to deliver pacing therapy and provide for anodal stimulation detection and/or mitigation/elimination in accordance with embodiments of the invention. The components, functionality, and configurations depicted are intended to provide an understanding of various features and combinations of features that may be incorporated in such a system. It is understood that a wide variety of device configurations are contemplated, ranging from relatively sophisticated to relatively simple designs. As such, particular configurations may include some components illustrated in FIG. 10, while excluding other components. In certain embodiments, the arrangement of the functional blocks may vary from the arrangement depicted.

The system illustrated in FIG. 10 provides functionality for performing anodal stimulation detection and mitigating same. The system shown in FIG. 10 may also provide for trending of anodal stimulation data and display of trended data. In some configurations, anodal stimulation detection and mitigation of same may be performed entirely by the implantable CRM device or in cooperation with a programmer, a remote server, or other external device. In yet other embodiments, the functionality may be divided between a patient implantable device and a patient external device.

The therapy system 700 illustrated in FIG. 10 includes a therapy control processor 740 configured to control pacing therapy circuitry 730 to generate pacing stimulations applied via the cardiac electrodes 725. The therapy control processor 740 may also control high energy shocks produced by the defibrillation/cardioversion circuitry 735 for treating tachyarrhythmia.

Cardiac signals are sensed using cardiac electrodes 725. The sensed cardiac signals are received by sensing circuitry 720, which includes circuitry and for amplifying, filtering and/or digitizing the cardiac signals. The sensed cardiac signals may optionally be processed by noise reduction circuitry (not shown), which may reduce noise and or increase the signal to noise ratio (SNR) of the signals before signals are sent to the control processor 740.

Circuitry 720 may be configured to detect various cardiac signal features, such as R-waves, A-waves, QRS complexes, Q* deflections, His bundle activations, and/or other cardiac signal features. Circuitry 720 may also be configured to measure intrinsic conduction intervals and other cardiac intervals, including intrinsic atrioventricular intervals (left and/or right), QRS widths, A-A intervals, V-V intervals and/or other cardiac intervals. Information from circuitry 720 is input to a therapy control processor 740. Using conduction information from circuitry 720, the optimization circuitry 775 calculates optimal pacing delays. Pacing interval controller 765 times the optimal pacing delays which are initiated responsive to specific cardiac events, e.g., Q* and/or His bundle activation.

The therapy control processor 740 includes an anodal stimulation detector 775 that operates in a manner described hereinabove. A pacing parameter controller 765 adjusts LV pace parameters and, if necessary, pacing vector selection to mitigate or eliminate detected anodal stimulation. The therapy control processor 740 may include arrhythmia detection circuitry such as a signal processor that coordinates analysis of the sensed cardiac signals and/or other sensor inputs to detect cardiac tachyarrhythmia. Rate based and/or morphological discrimination algorithms may be implemented by the control processor 740 to detect and verify the presence and severity of an arrhythmic episode. If arrhythmia is detected, the therapy control processor 740 may coordinate delivery of an appropriate therapy, such as anti-tachyarrhythmia pacing therapy (ATP), cardioversion, and/or defibrillation via the defibrillation/cardioversion circuitry 735 to terminate or mitigate the arrhythmia.

Communications circuitry 750 is coupled to the control processor 740. The communications circuitry 750 allows communication between devices, such as patient-external devices 755 and patient-implantable devices. In one configuration, the communications circuitry 750 and the patient-external device 755 use a wire loop antenna and a radio frequency telemetric link, as is known in the art, to receive and transmit signals and data between the patient-external device 755 and communications circuitry 750. In this manner, programming commands and data may be transferred to the control processor 740 from the patient-external device 755 during and after implant. Using a patient-external programmer, a physician is able to set or modify various parameters used by the therapy control processor 740. For example, a physician may set or modify parameters affecting monitoring, detection, pacing, and defibrillation functions of the therapy control processor 740.

In certain embodiments, the control processor 740 transmits information for determination of pacing timing to the patient-external device 755. The information may include, for example, cardiac electrical signals, markers indicating the timing of certain features or points, measured characteristics or features of the signals, and/or other information. The patient-external device 755 may use the transmitted information to determine pacing timing intervals or may format and display information to facilitate the determination of pacing delays by a human analyst.

Anodal stimulation data, such as any of the data described above that is acquired and/or produced by the control processor 740, can be communicated to the patient-external device 755 and subject to various known trending algorithms. For example, anodal stimulation data may be transmitted to an APM system and subject to processing by various trending algorithms implemented on an APM system processor. Trending algorithms may also or alternatively be implemented by the control processor 740 of the therapy device 700 (e.g., CRT-P or CRT-D device). Trending and other data may be displayed on a display of the APM system or a programmer (e.g., a display of the patient-external device 755).

Processes for timing the delivery of pace pulses based on early activation in accordance with some embodiments of the invention may be implemented by an implantable device, by a patient-external device, such as a programmer or advanced patient management system, or by a manually implementable procedure, such as by using a printed table lookup to compute the optimal values, and/or by any combination of these techniques.

In one embodiment, the patient-external programmer 755 communicates with the control processor 740 over a telemetry link and receives either raw electrogram data, markers corresponding to particular sensed events, and/or measurements of intervals between sensed events or feature widths as computed by the implantable device. The external programmer 755 may then compute optimal settings for pacing timing intervals which are either transmitted to the control processor 740 for immediate reprogramming or presented to a clinician operating the external programmer as recommendations.

In another embodiment, the external programmer 755 may present the data, markers, anodal stimulation data/trends and/or measurements to a human analyst who then programs the control processor 740 in accordance with an algorithm. In yet a further embodiment, determination of the pacing timing may be fully automatic and performed by an implantable therapy device.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A cardiac resynchronization therapy system, comprising:
   an implantable lead system comprising left and right ventricular electrodes configurable in at least an extended bipolar configuration and at least an alternative bipolar or unipolar configuration differing from the extended bipolar configuration, at least one left ventricular electrode defining a cathode of the extended bipolar configuration and a right ventricular electrode defining an anode of the extended bipolar configuration;
   energy delivery circuitry coupled to the lead system;
   sensing circuitry coupled to the lead system;
   a controller coupled to the sensing circuitry and the energy delivery circuitry, the controller configured to execute program instructions for sensing cardiac electrical activity and delivering cardiac resynchronization therapy (CRT) to the heart in accordance with programmed pacing parameters including a non-zero intraventricular delay (IVD), the controller configured to deliver a pace pulse to the at least one left ventricular electrode defining the cathode of the extended bipolar configuration;
   a detector coupled to the sensing circuitry and the controller, the detector configured to sense for a response to the pace pulse and detect anodal stimulation of the right ventricle based on the sensed response; and
   the controller is configured to selectably switch from a current extended bipolar pace vector to an alternative bipolar or unipolar pace vector without ganging an additional anode electrode with the right ventricular electrode to mitigate or eliminate detected anodal stimulation of the right ventricle.

2. The system of claim 1, wherein the anode of the current extended bipolar pace vector comprises a single right ventricular ring electrode, and the cathode of the current extended bipolar pace vector comprises at least one of a left ventricular ring electrode or a left ventricular tip electrode.

3. The system of claim 1, wherein the lead system comprises a multiple-pole left ventricular lead comprising a plurality of the left ventricular ring electrodes, at least one of the electrodes of the multiple-pole left ventricular lead defining the cathode of the current extended bipolar pace vector and the anode of the current extended bipolar pace vector comprising a single right ventricular ring electrode.

4. The system of claim 1, wherein the controller is configured to switch from the current extended bipolar pace vector to an alternative unipolar pace vector that excludes the right ventricular electrode and includes at least one left ventricular electrode.

5. The system of claim 1, wherein the controller is configured to switch from the current extended bipolar pace vector to the alternative bipolar pace vector, the alternative bipolar pace vector comprising at least one left ventricular pacing electrode.

6. The system of claim 1, wherein the controller is configured to switch from the current extended bipolar pace vector to the alternative bipolar or unipolar pace vector, the alternative bipolar or unipolar pace vector comprising at least one left ventricular pacing electrode.

7. The system of claim 1, wherein the controller is configured to switch from the current extended bipolar pace vector to the alternative bipolar pace vector, the alternative bipolar pace vector comprising an extended bipolar pacing electrode configuration differing from the current extended bipolar configuration and comprising at least one left ventricular pacing electrode.

8. The system of claim 7, wherein the controller is configured to switch from the current extended bipolar pace vector to the alternative extended bipolar pace vector.

9. The system of claim 1, wherein the detector is configured to detect presence or absence of an expected right ventricular (RV) sense after a predetermined delay following delivery of the LV pace pulse, wherein presence of the expected RV sense detected after the predetermined delay is indicative of an absence of anodal stimulation of the right ventricle and non-detection of the expected RV sense after the predetermined delay is indicative of anodal stimulation of the right ventricle.

10. The system of claim 1, comprising memory configured to store an expected evoked response template indicative of left ventricular capture responsive to left ventricular pacing using a bipolar or unipolar electrode configuration, wherein the controller is configured to generate a second template indicative of left ventricular capture responsive to left ventricular pacing using the extended bipolar configuration and the detector is configured to detect presence or absence of right ventricular anodal stimulation based on a comparison of the expected evoked response template and the second template.

11. The system of claim 1, wherein the controller is configured to enable a right ventricular capture verification test during a left ventricular threshold test.

12. The system of claim 1, wherein the controller is configured to deliver a predetermined number of left ventricular pace pulses using the extended bipolar configuration and the detector is configured to detect a number of right ventricular capture events responsive to the predetermined number of left ventricular pace pulses, the detector configured to detect right ventricular anodal stimulation based on a comparison of the number of right ventricular capture events relative to the predetermined number of left ventricular pace pulses.

13. The system of claim 1, wherein the detector is configured to detect right ventricular anodal stimulation during a left ventricular capture threshold test.

14. The system of claim 1, wherein the controller is configured to implement a left ventricular (LV) capture threshold test using the extended bipolar configuration, the detector is configured to detect LV capture and right ventricular (RV) anodal stimulation during the LV capture threshold test and determine an LV capture threshold value and an RV anodal stimulation threshold value.

15. The system of claim 1, wherein the detector is configured to detect right ventricular (RV) anodal stimulation resulting from a left ventricular (LV) test pace based on a comparison of:
  an LV evoked response template developed from LV responses to a predetermined number of LV paces during extended bipolar pacing; and
  an expected LV evoked response morphological template developed from LV responses to a predetermined number of LV paces during bipolar or unipolar LV pacing.

16. The system of claim 1, wherein the detector is configured to detect fusion or non-capture based on a comparison of:
  a left ventricular (LV) evoked response template developed from LV responses to a predetermined number of LV paces that do not result in right ventricular anodal stimulation; and
  a second LV evoked response template developed from LV responses to a predetermined number of LV paces that result in right ventricular anodal stimulation.

17. The system of claim 1, wherein the controller is configured to implement a left ventricular (LV) capture threshold test using the extended bipolar configuration, the detector configured to detect LV capture, right ventricular (RV) anodal stimulation, and fusion/non-capture during the LV capture threshold test and determine an LV capture threshold value and an RV anodal stimulation threshold value.

18. A method of delivering cardiac resynchronization therapy, comprising:
  selectably delivering cardiac resynchronization therapy (CRT) to a heart using at least an extended bipolar electrode configuration and at least an alternative bipolar or unipolar electrode configuration differing from the extended bipolar electrode configuration in accordance with programmed pacing parameters including a non-zero intraventricular delay (IVD), the extended bipolar electrode configuration comprising at least a left ventricular electrode defining a cathode of the extended bipolar electrode configuration and a single right ventricular electrode defining an anode of the extended bipolar electrode configuration;
  delivering a pace pulse to the left ventricular electrode;
  sensing for a response to the pace pulse;
  detecting anodal stimulation of the right ventricle based on the sensed response; and
  switching from a current extended bipolar pace vector to an alternative bipolar or unipolar pace vector without ganging an additional anode electrode with the single right ventricular electrode to mitigate or eliminate detected anodal stimulation of the right ventricle.

19. The method of claim 18, wherein:
- the anode of the current extended bipolar pace configuration comprises the single right ventricular ring electrode;
- the cathode of the current extended bipolar pace configuration comprises at least one left ventricular pace electrode; and
- the alternative bipolar pace configuration comprises at least one left ventricular pace electrode.

20. The method of claim 18, wherein switching from the current extended bipolar pace vector to the alternative bipolar pace vector comprises switching to an alternative extended bipolar pace vector differing from the current extended bipolar pace vector and comprising at least one left ventricular pace electrode.

21. The method of claim 18, wherein switching from the current extended bipolar pace vector to the alternative unipolar pace vector comprises switching to the alternative unipolar pace vector that includes at least one left ventricular electrode and excludes the single right ventricular electrode.

22. The method of claim 18, comprising:
- storing an expected evoked response template indicative of left ventricular capture responsive to left ventricular pacing using a bipolar or unipolar electrode configuration;
- generating a second template indicative of left ventricular capture responsive to left ventricular pacing using the extended bipolar electrode configuration; and
- detecting presence or absence of right ventricular anodal stimulation based on a comparison of the expected evoked response template and the second template.

23. The method of claim 18, comprising:
- comparing a left ventricular (LV) evoked response template, developed from LV responses to a predetermined number of LV paces during extended bipolar pacing, to an expected LV evoked response morphological template developed from LV responses to a predetermined number of LV paces during bipolar or unipolar LV pacing; and
- detecting right ventricular anodal stimulation resulting from an LV test pace based on the comparison.

24. The method of claim 18, comprising:
- comparing a left ventricular (LV) evoked response template, developed from LV responses to a predetermined number of LV paces that do not result in right ventricular anodal stimulation, to a second LV evoked response template developed from LV responses to a predetermined number of LV paces that result in right ventricular anodal stimulation; and
- detecting fusion or non-capture based on the comparison.

25. The method of claim 18, comprising:
- comparing a left ventricular (LV) evoked response template, developed from LV responses to a predetermined number of LV paces that do not result in right ventricular anodal stimulation, and a second LV evoked response template, developed from LV responses to a predetermined number of LV paces that result in right ventricular anodal stimulation; and
- detecting fusion or non-capture based on the comparison.

26. The method of claim 18, comprising:
- implementing a left ventricular (LV) capture threshold test using the extended bipolar configuration; and
- detecting LV capture, right ventricular anodal stimulation, and one or both of fusion and non-capture during the LV capture threshold test; and
- determining an LV capture threshold value and an RV anodal stimulation threshold value.

27. The method of claim 18, comprising:
- modifying one or more left ventricular (LV) pacing parameters to mitigate or eliminate detected anodal stimulation of the right ventricle without physician intervention of left ventricular pacing parameter modification; and
- switching from the current extended bipolar pace vector to an alternative bipolar or unipolar pace vector in response of LV pacing parameter modification failing to mitigate or eliminate detected anodal stimulation of the right ventricle.

28. A system for delivering cardiac resynchronization therapy, comprising:
- means for selectably delivering cardiac resynchronization therapy (CRT) to a heart using at least an extended bipolar electrode configuration and at least an alternative bipolar or unipolar electrode configuration differing from the extended bipolar electrode configuration in accordance with programmed pacing parameters including a non-zero intraventricular delay (IVD), the extended bipolar electrode configuration comprising at least a left ventricular electrode defining a cathode of the extended bipolar electrode configuration and a single right ventricular electrode defining an anode of the extended bipolar electrode configuration;
- energy delivery circuitry configured to deliver a pace pulse to the left ventricular electrode;
- sensing circuitry configured to sense for a response to the pace pulse;
- means for detecting anodal stimulation of the right ventricle based on the sensed response; and
- means for switching from a current extended bipolar pace vector to an alternative bipolar or unipolar pace vector without ganging an additional anode electrode with the right ventricular electrode to mitigate or eliminate detected anodal stimulation of the right ventricle.

* * * * *